(12) United States Patent
Hayashi

(10) Patent No.: US 12,064,180 B2
(45) Date of Patent: Aug. 20, 2024

(54) DISPLAY APPARATUS, DISPLAY METHOD, AND DISPLAY PROGRAM

(71) Applicant: JVCKENWOOD Corporation, Yokohama (JP)

(72) Inventor: Takahiro Hayashi, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 449 days.

(21) Appl. No.: 17/458,683

(22) Filed: Aug. 27, 2021

(65) Prior Publication Data

US 2021/0386283 A1 Dec. 16, 2021

Related U.S. Application Data

(63) Continuation of application No. PCT/JP2019/044445, filed on Nov. 12, 2019.

(30) Foreign Application Priority Data

Mar. 8, 2019 (JP) ................................ 2019-042988

(51) Int. Cl.
*A61B 3/00* (2006.01)
*A61B 3/113* (2006.01)

(52) U.S. Cl.
CPC .......... *A61B 3/0091* (2013.01); *A61B 3/0041* (2013.01); *A61B 3/113* (2013.01)

(58) Field of Classification Search
CPC ...... A61B 3/0041; A61B 3/0091; A61B 3/113
See application file for complete search history.

(56) References Cited

U.S. PATENT DOCUMENTS

| 2014/0253876 A1 | 9/2014 | Klin et al. |
| 2016/0209917 A1 | 7/2016 | Cerriteno et al. |
| 2019/0073024 A1 | 3/2019 | Komurata et al. |
| 2020/0069230 A1 | 3/2020 | Shudo |

FOREIGN PATENT DOCUMENTS

| EP | 0055338 | 7/1982 |
| JP | 2012-234405 | 11/2012 |
| JP | 2017-158868 | 9/2017 |
| JP | 2018-192195 | 12/2018 |
| WO | 2017/031089 | 2/2017 |
| WO | 2017/213070 | 12/2017 |

OTHER PUBLICATIONS

International Search Report and Written Opinion for International Application No. PCT/JP2019/044445 mailed on Jan. 21, 2020, 8 pages.
Extended European Search Report for European Patent Application No. 19918516.6 mailed Feb. 28, 2022.

*Primary Examiner* — Jack Dinh
(74) *Attorney, Agent, or Firm* — Amin, Turocy & Watson, LLP

(57) ABSTRACT

A display apparatus includes a display unit that displays a predetermined target object to be gazed at by a subject, a gaze point detection unit that detects a position of a gaze point of the subject who observes the display unit, a region setting unit that sets a specific region corresponding to the predetermined target object, a determination unit that determines whether the gaze point is present in the specific region, an arithmetic unit that calculates gaze point data on the basis of a determination result of the determination unit, and a display control unit that displays an index at a position corresponding to the gaze point on the display unit if the gaze point data meets a predetermined index display condition.

4 Claims, 10 Drawing Sheets

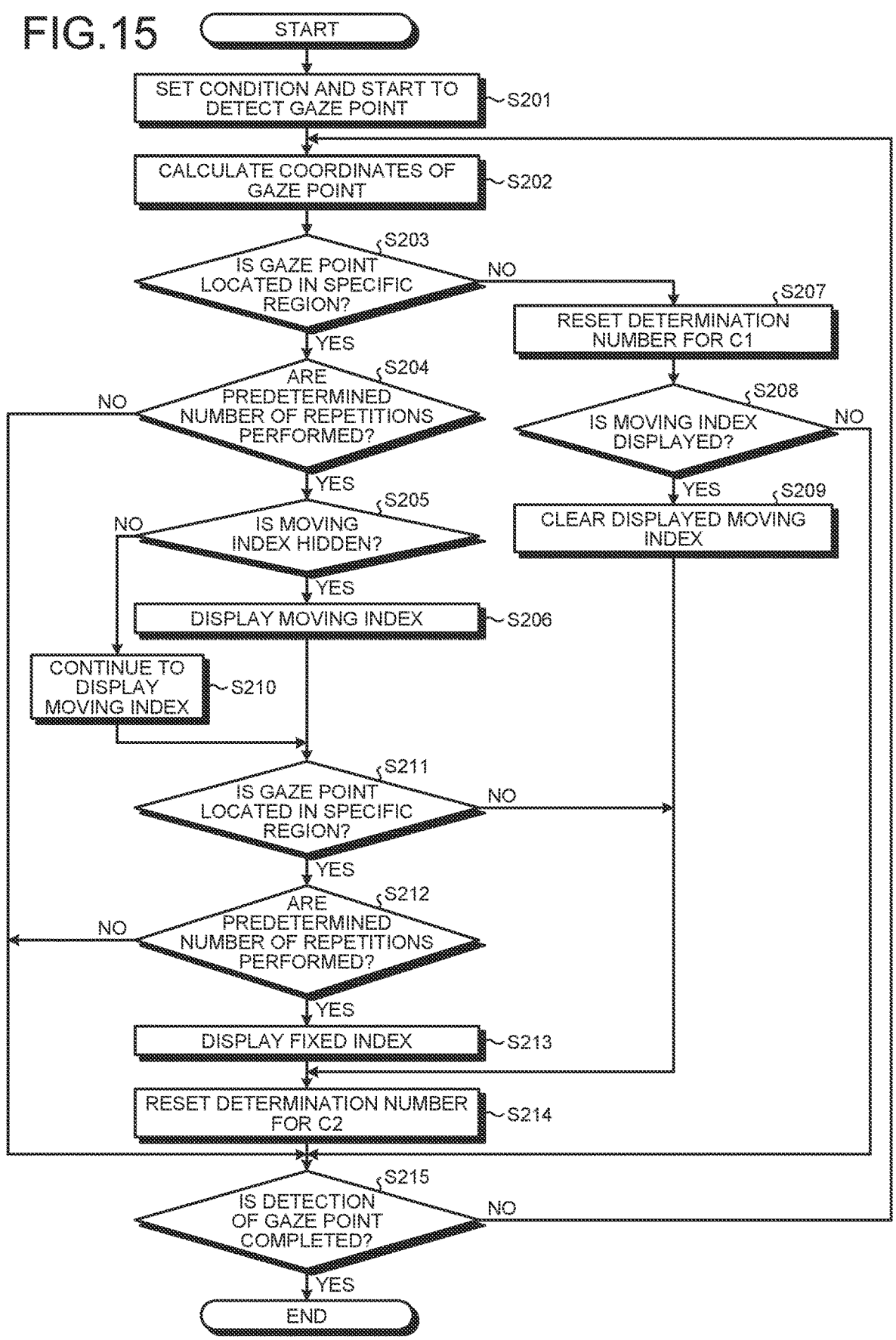

DISPLAY APPARATUS, DISPLAY METHOD, AND DISPLAY PROGRAM

CROSS-REFERENCE TO RELATED APPLICATION(S)

This application is a Continuation of PCT international application Ser. No. PCT/JP2019/044445 filed on Nov. 12, 2019 which designates the United States, incorporated herein by reference, and which claims the benefit of priority from Japanese Patent Application No. 2019-42988, filed on Mar. 8, 2019, incorporated herein by reference.

BACKGROUND

1. Technical Field

The present disclosure relates to a display apparatus, a display method, and a display program.

2. Description of the Related Art

Visual cognitive functions include a function to input information from eyes and a function to recognize the input information. In the function to input information from eyes, visual performance, such as eye movement, for looking at a target object is important. As a method of evaluating the visual performance, for example, a technology for displaying a graphic on a display unit, requesting a subject to gaze at the graphic, detecting a position of a gaze point, and calculating a gaze time in a predetermined region of the graphic has been disclosed (for example, see Japanese Laid-open Patent Publication No. 2017-158868 A).

In the technology described in Japanese Laid-open Patent Publication No. 2017-158868 A, a technology for detecting the gaze point of the subject, calculating the gaze time, and performing evaluation by an evaluator is described. However, in the technology described in Japanese Laid-open Patent Publication No. 2017-158868 A, while evaluation of the visual performance of the subject is described, feedback on a state of the visual performance to the subject is not described.

SUMMARY

It is an object of the present disclosure to at least partially solve the problems in the conventional technology.

A display apparatus according to the present disclosure comprising: a display unit that displays a predetermined target object to be gazed at by a subject; a gaze point detection unit that detects a position of a gaze point of the subject who observes the display unit; a region setting unit that sets a specific region corresponding to the predetermined target object; a determination unit that determines whether the gaze point is present in the specific region; an arithmetic unit that calculates gaze point data on the basis of a determination result of the determination unit; and a display control unit that, if the gaze point data meets a predetermined index display condition, displays an index at a position corresponding to a gaze point of the subject on the display unit in a period in which the gaze point detection unit is detecting a position of a gaze point of the subject.

A display method according to the present disclosure comprising: displaying a predetermined target object to be gazed at by a subject on a display unit; detecting a position of a gaze point of the subject who observes the display unit; setting a specific region corresponding to the predetermined target object; determining whether the gaze point is present in the specific region; calculating gaze point data on the basis of a determination result; and displaying, if the gaze point data meets a predetermined index display condition, an index at a position corresponding to a gaze point of the subject on the display unit in a period in which a position of a gaze point of the subject is being detected.

A non-transitory computer readable recording medium storing therein a display program according to the present disclosure that causes a computer to execute: a process of displaying a predetermined target object to be gazed at by a subject on a display unit; a process of detecting a position of a gaze point of the subject who observes the display unit; a process of setting a specific region corresponding to the predetermined target object; a process of determining whether the gaze point is present in the specific region; a process of calculating gaze point data on the basis of a determination result; and a process of displaying, if the gaze point data meets a predetermined index display condition, an index at a position corresponding to a gaze point of the subject on the display unit in a period in which a position of a gaze point of the subject is being detected.

BRIEF DESCRIPTION OF THE DRAWINGS

FIG. 15 is a flowchart illustrating another example of the display method according to the present embodiment.

DETAILED DESCRIPTION OF THE PREFERRED EMBODIMENTS

Embodiments of a display apparatus, a display method, and a display program according to the present disclosure will be described below based on the drawings. The disclosure is not limited by the embodiments below. In addition, structural elements in the embodiments described below include one that can easily be thought of by a person skilled in the art and one that is practically identical.

In the description below, the three-dimensional global coordinate system is set to describe positional relationships between components. A direction parallel to a first axis of a predetermined plane will be referred to as an X-axis direction, a direction parallel to a second axis of the predetermined plane perpendicular to the first axis will be referred to as an Y-axis direction, and a direction parallel to a third axis perpendicular to each of the first axis and the second axis will be referred to as a Z-axis direction. The predetermined plane includes an XY plane.

Display Apparatus

Figure 1:
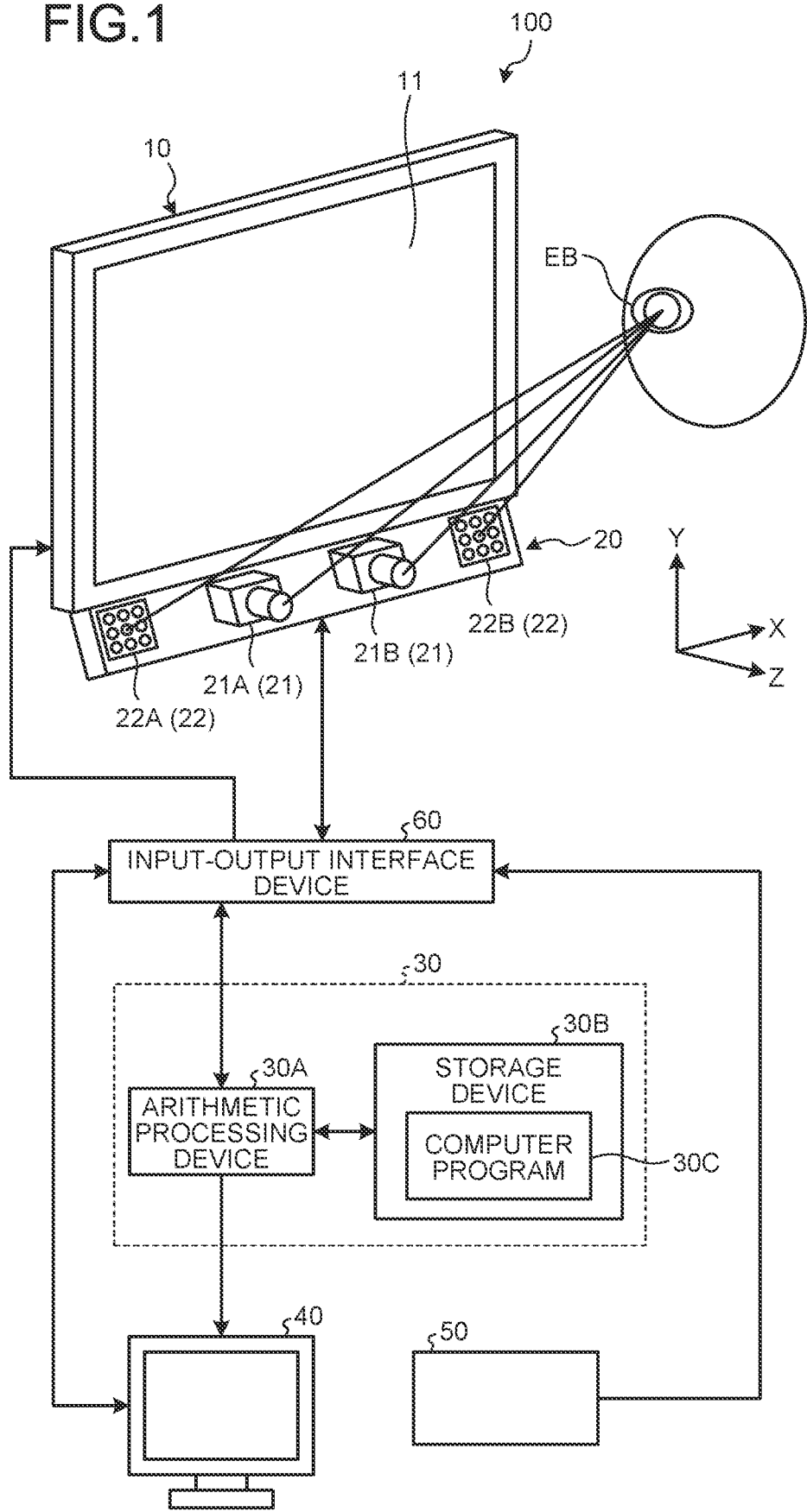
FIG. 1 is a diagram schematically illustrating an example of a display apparatus according to the present embodiment.

FIG. 1 is a diagram schematically illustrating an example of a display apparatus 100 according to the present embodiment. The display apparatus 100 according to the present embodiment detects a line of sight of a subject, and gives feedback on a state of visual performance to the subject by using a detection result. As the display apparatus 100, various apparatuses capable of detecting a line of sight of a subject, such as an apparatus that detects the line of sight on the basis of a position of a pupil of the subject and a position of a corneal reflection image and an apparatus that detects the line of sight on the basis of a position of an inner corner of an eye of the subject and a position of an iris of the subject, may be used, for example.

As illustrated in FIG. 1, the display apparatus 100 includes a display device 10, an image acquisition device 20, a computer system 30, an output device 40, an input device 50, and an input-output interface device 60. The display device 10, the image acquisition device 20, the computer system 30, the output device 40, and the input device 50 perform data communication via the input-output interface device 60. Each of the display device 10 and the image acquisition device 20 includes a driving circuit (not illustrated).

The display device 10 includes a flat panel display, such as a liquid crystal display (LCD) or an organic electroluminescence display (OLED). In the present embodiment, the display device 10 includes a display unit 11. The display unit 11 displays information, such as an image. The display unit 11 is substantially parallel to the XY plane. The X-axis direction is a horizontal direction of the display unit 11, the Y-axis direction is a vertical direction of the display unit 11, and the Z-axis direction is a depth direction perpendicular to the display unit 11. The display device 10 may be a head mounted display device. If the display device 10 is a head mounted display device, a component like the image acquisition device 20 is arranged in a head mounted module.

The image acquisition device 20 acquires image data of left and right eyeballs EB of the subject, and transmits the acquired image data to the computer system 30. The image acquisition device 20 includes an imaging device 21. The imaging device 21 captures images of the left and right eyeballs EB of the subject and acquires image data. The imaging device 21 includes various cameras corresponding to methods of detecting the line of sight of the subject. For example, if a method of detecting the line of sight based on a position of a pupil of the subject and a position of a corneal reflection image is adopted, the imaging device 21 includes an infrared camera, an optical system capable of transmitting near-infrared light at a wavelength of 850 nm, and an imaging element capable of receiving the near-infrared light, for example. Further, for example, if a method of detecting the line of sight based on a position of an inner corner of an eye of the subject and a position of an iris of the subject is adopted, the imaging device 21 includes a visible light camera. The imaging device 21 outputs a frame synchronous signal. A cycle of the frame synchronous signal may be, for example, 20 milliseconds (msec), but is not limited thereto. The imaging device 21 may be configured as, for example, a stereo camera including a first camera 21A and a second camera 21B, but is not limited thereto.

Furthermore, for example, if the method of detecting the line of sight based on the position of the pupil of the subject and the position of the corneal reflection image is adopted, the image acquisition device 20 includes a lighting device 22 that illuminates the eyeballs EB of the subject. The lighting device 22 includes a light emitting diode (LED) light source, for example, and is able to emit near-infrared light at a wavelength of 850 nm. Meanwhile, for example, if a method of detecting a line-of-sight vector based on the position of the inner corner of the eye of the subject and the position of the iris of the subject is adopted, the lighting device 22 may be omitted. The lighting device 22 emits detection light in synchronization with the frame synchronous signal of the imaging device 21. The lighting device 22 may include, for example, a first light source 22A and a second light source 22B, but is not limited thereto.

The computer system 30 integrally controls operation of the display apparatus 100. The computer system 30 includes an arithmetic processing device 30A and a storage device 30B. The arithmetic processing device 30A includes a microprocessor, such as a central processing unit (CPU). The storage device 30B includes a memory, such as a read only memory (ROM) and a random access memory (RAM), or a storage. The arithmetic processing device 30A performs an arithmetic process in accordance with a computer program 30C that is stored in the storage device 30B.

The output device 40 includes a display device, such as a flat panel display. Meanwhile, the output device 40 may include a printing device. The input device 50 generates input data by being operated. The input device 50 includes a keyboard or a mouse for a computer system. Meanwhile, the input device 50 may include a touch sensor that is arranged on a display unit of the output device 40 that is a display device.

In the display apparatus 100 according to the present embodiment, the display device 10 and the computer system 30 are separate devices. Meanwhile, the display device 10 and the computer system 30 may be integrated. For example, the display apparatus 100 may include a tablet personal computer. In this case, the display device, the image acquisition device, the computer system, the input device, the output device, and the like may be mounted on the tablet personal computer.

Figure 2:
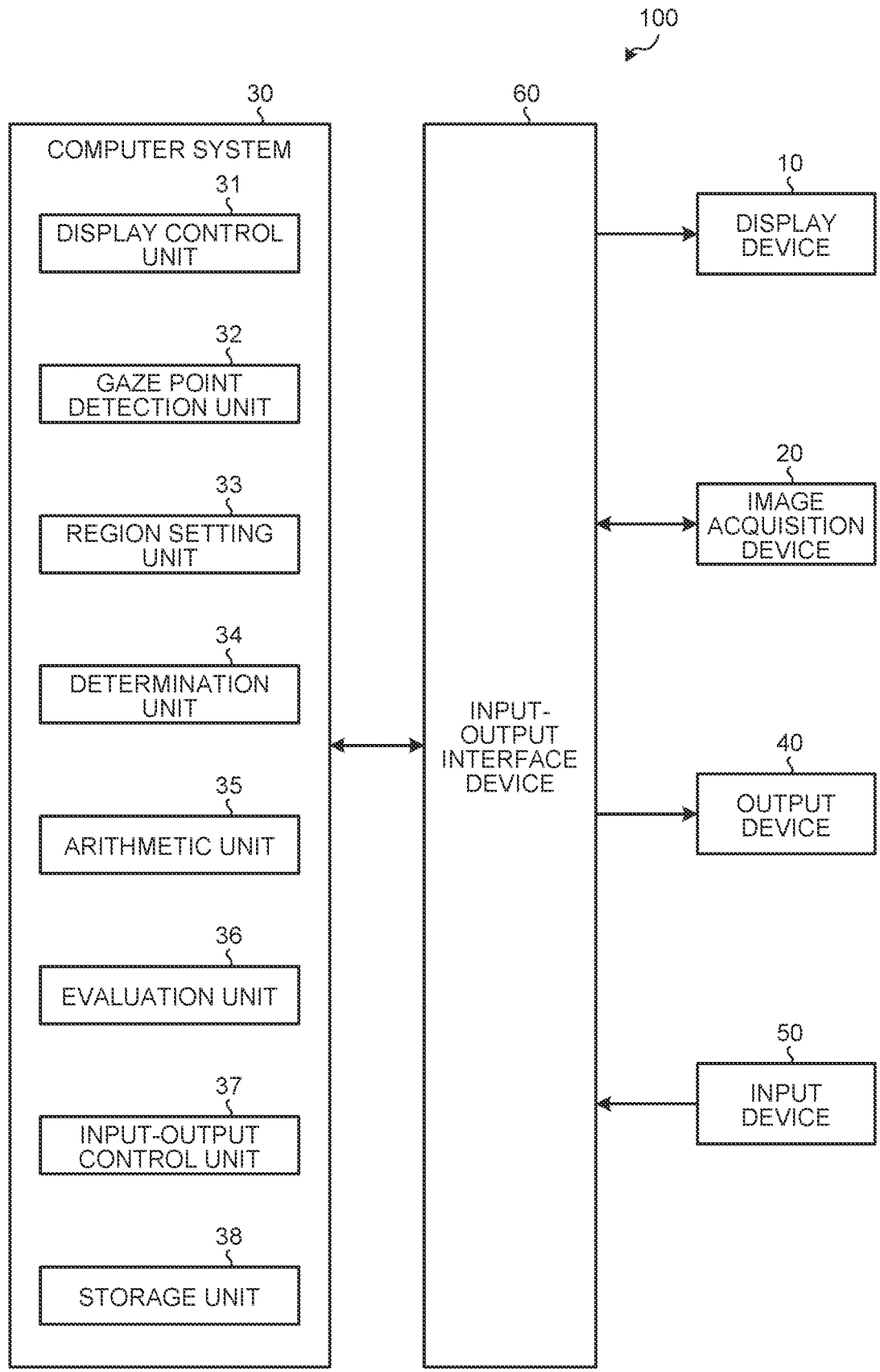
FIG. 2 is a functional block diagram illustrating an example of the display apparatus.

FIG. 2 is a functional block diagram illustrating an example of the display apparatus 100. As illustrated in FIG. 2, the computer system 30 includes a display control unit 31, a gaze point detection unit 32, a region setting unit 33, a determination unit 34, an arithmetic unit 35, an evaluation unit 36, an input-output control unit 37, and a storage unit 38. Functions of the computer system 30 are implemented by the arithmetic processing device 30A and the storage device 30B (see FIG. 1). Meanwhile, a part of the functions of the computer system 30 may be arranged outside the display apparatus 100.

The gaze point detection unit 32 detects positional data of a gaze point of the subject. In the present embodiment, the gaze point detection unit 32 detects a line-of-sight vector of the subject defined by the three-dimensional global coordinate system, on the basis of the image data of the left and right eyeballs EB of the subject acquired by the image acquisition device 20. The gaze point detection unit 32 detects positional data of an intersection of the detected line-of-sight vector of the subject and the display unit 11 of the display device 10, as the positional data of the gaze point of the subject. In other words, in the present embodiment, the positional data of the gaze point is the positional data of the intersection of the line-of-sight vector of the subject and the display unit 11 of the display device 10 defined by the three-dimensional global coordinate system. In the present embodiment, the gaze point is a designated point that is designated on the display unit 11 by being gazed at by the subject. The gaze point detection unit 32 detects the positional data of the gaze point of the subject for each prescribed sampling cycle. The sampling cycle may be, for example, the cycle (for example, every 20 msec) of the frame synchronous signal output from the imaging device 21.

The region setting unit 33 sets specific regions in the display unit 11. The specific regions may have various planner shapes, such as circles, ellipses, polygons, or combinational shapes of circles, ellipses, and polygons, for example. The region setting unit 33 may set the specific regions in the entire display unit 11 or may set the specific regions in a part of the display unit 11. In the present embodiment, each of the regions set by the region setting unit 33 is not displayed on the display unit 11 in principle. Meanwhile, each of the regions may be displayed on the display unit 11 under the control of the display control unit 31, for example.

The determination unit 34 determines whether the gaze point is present in a specific region in a period in which the region setting unit 33 sets the specific region, and outputs determination data. The determination unit 34 determines whether the gaze point is present in the specific region for each prescribed determination cycle. The determination cycle may be, for example, the same cycle as the cycle (for example, every 20 msec) of the frame synchronous signal output from the imaging device 21. In this case, the determination cycle of the determination unit 34 is the same as the sampling cycle of the gaze point detection unit 32.

The arithmetic unit 35 calculates gaze point data that indicates a course of movement of the gaze point in the period in which the specific region is set as described above, on the basis of the determination data of the determination unit 34. The arithmetic unit 35 calculates presence time data as the gaze point data, for example. The presence time data is data that indicates presence time in which the gaze point is present in the specific region. It is possible to estimate that the presence time in which the gaze point is present in the specific region increases with an increase in the number of times that the determination unit 34 determines that the gaze point is present in the specific region. Therefore, in the present embodiment, it is assumed that the presence time is the number of times of determination made by the determination unit 34. In other words, it is assumed that the presence time is the number of samplings of gaze points detected in the specific region. The arithmetic unit 35 includes a counter that counts the number of times that the determination unit 34 determines that the gaze point is present in the specific region.

The display control unit 31 displays an evaluation image for evaluating visual performance of the subject on the display unit 11. A display mode of the evaluation image may be any of a moving image and a still image. Further, if the gaze point data meets an index display condition, the display control unit 31 displays an index at a position corresponding to the gaze point on the display unit 11. In this case, if the presence time is equal to or larger than a predetermined time as the index display condition, the display control unit 31 displays the index on the display unit 11.

The index includes, for example, a moving index and a fixed index. The moving index is displayed at the position of the gaze point every time the gaze point detection unit 32 detects the gaze point. In other words, the moving index is displayed at a position of a sampled gaze point every time the gaze point detection unit 32 performs sampling. The fixed index is displayed at the position of the gaze point at the time the gaze point data meets the index display condition. In other words, the fixed index is displayed at a position of a gaze point that meets the index display condition.

As an external appearance of the index, the index may have various shapes, such as a circle, an ellipse, a polygon, or a combinational shape of a circle, an ellipse, and a polygon, for example. Further, the shape of the index is not limited to a geometric shape, and may be an image representing an animal, a plant, or the like. As the external appearance of the index, the index may have any color as long as the color is displayable on the display unit 11, and may have a single color or a mixed color of a plurality of colors, for example. As the external appearance of the index, the index may have any size as long as the size is displayable on the display unit 11, for example. The display control unit 31 hides the index if the gaze point data does not meet the index display condition while the index is being displayed on the display unit 11. The index as described above is stored, as index data, in the storage unit 38.

The evaluation unit 36 obtains evaluation data of the subject on the basis of the gaze point data. The evaluation data includes, for example, data for evaluating whether the subject is able to gaze at a predetermined region in the evaluation image displayed on the display unit 11.

The input-output control unit 37 acquires data (the image data of the eyeballs EB, the input data, or the like) from at least one of the image acquisition device 20 and the input device 50. Further, the input-output control unit 37 outputs data to at least one of the display device 10 and the output device 40. The input-output control unit 37 may output a task for the subject from the output device 40, such as a speaker.

The storage unit 38 stores therein the determination data, the gaze point data (the presence time data), and the index data as described above. Further, the storage unit 38 stores therein a display program that causes a computer to perform a process of detecting positions of gaze points of the subject who observes the display unit 11, a process of setting a specific region in the display unit 11, a process of determining whether each of the gaze points is present in the specific region, a process of calculating the gaze point data on the basis of a determination result, and a process of displaying an index at a position corresponding to the gaze point on the display unit 11 if the gaze point data meets the index display condition.

Display Method

A display method according to the present embodiment will be described below. In the display method according to the present embodiment, feedback on a state of visual performance is given to the subject by using the display apparatus 100 as described above.

Figure 3:
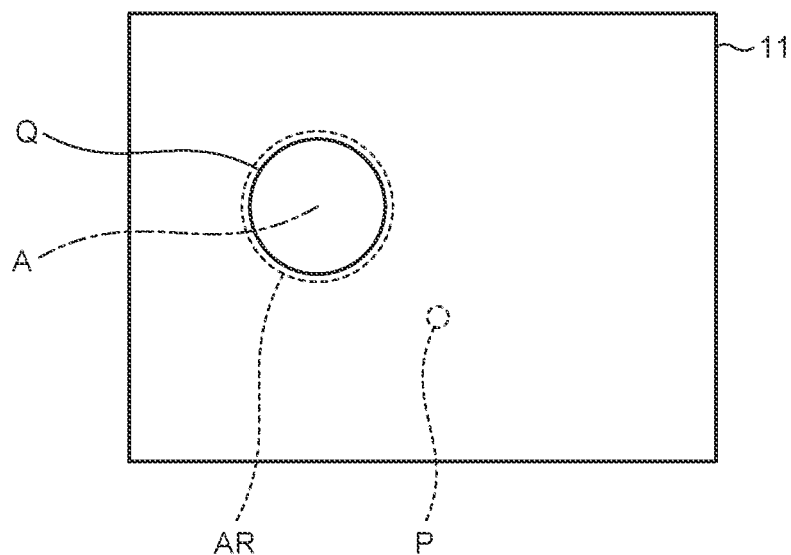
FIG. 3 is a diagram illustrating an example of contents displayed on a display unit.

FIG. 3 is a diagram illustrating an example of contents displayed on the display unit 11. The display control unit 31 displays the evaluation image for evaluating the visual performance of the subject on the display unit 11. The display control unit 31 displays, for example, a target object Q on the display unit 11. The target object Q has, for example, a circular shape. Meanwhile, it is possible to cause the display unit 11, the output device 40, or the like to give, in advance, an instruction to gaze at the target object Q for a while to the subject. Meanwhile, the target object Q need not always have a circular shape.

The region setting unit 33 sets a specific region AR corresponding to the target object Q. In the present embodiment, the specific region AR is a circle centered at a reference position A. Meanwhile, the specific region AR need not always have a circular shape, but may have a different shape. The reference position A may be, for example, a center position of the target object Q. The region setting unit 33 is able to set the specific region AR in a region including the target object Q, for example.

The gaze point detection unit 32 detects a position of a gaze point P of the subject on the display unit 11 for each prescribed sampling cycle (for example, 20 msec). While the position of the gaze point P detected by the gaze point detection unit 32 is represented by a dashed line on the display unit 11, the gaze point P is not displayed on the display unit 11 at the time as illustrated in FIG. 3. If the gaze point P is not displayed as described above, it is difficult for the subject to recognize a position at which the subject is gazing at. For example, if a position that the subject recognizes as a gaze position and a position of the detected gaze point are different, it is difficult to recognize deviation between the gaze position recognized by the subject and the position of the detected gaze point, so that, in some cases, a result indicating a gaze at a position that is different from the position recognized by the subject may be obtained.

In the present embodiment, the display control unit 31 displays an index at a position corresponding to the gaze point P on the display unit 11 if the gaze point data meets the index display condition. By allowing the subject to recognize a position at which the subject is gazing in real time, it is possible to give the subject an opportunity to correct the position of the gaze point P if the gaze position recognized by the subject and the position of the detected gaze point are different, for example.

The determination unit 34 determines whether the gaze point P is present in the specific region AR in a period in which the region setting unit 33 sets the specific region AR, and outputs determination data. The determination unit 34 determines whether the gaze point P is present in the specific region AR for each prescribed determination cycle. The determination cycle is the same as the sampling cycle of the gaze point detection unit 32.

The arithmetic unit 35 calculates the gaze point data that indicates a course of movement of the gaze point P in the period in which the specific region AR is set, on the basis of the determination data of the determination unit 34. The arithmetic unit 35 calculates the presence time data as the gaze point data, for example.

If the gaze point data meets the index display condition, the display control unit 31 displays the index at the position corresponding to the gaze point P on the display unit 11. In this case, if a first presence time is equal to or larger than a predetermined time as a first index display condition (hereinafter, described as a "first condition"), the display control unit 31 displays an index at the position corresponding to the gaze point on the display unit 11 every time the position of the gaze point is detected. The index is displayed on the display unit 11. The first condition may be that, for example, last 50 gaze points P are successively sampled in the specific region AR. Further, the index that is displayed when the first condition is met is the moving index.

Figure 4:
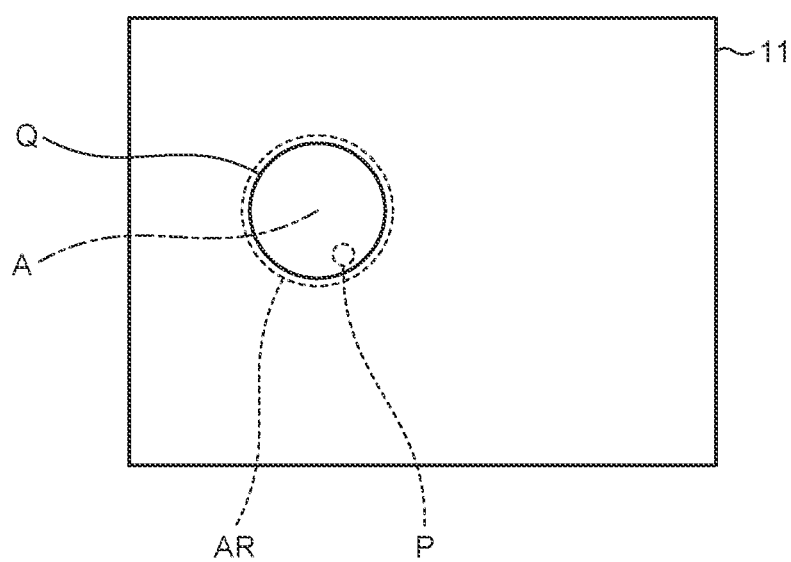
FIG. 4 is a diagram illustrating an example of contents displayed on the display unit.

FIG. 4 to FIG. 9 are diagrams illustrating examples of contents displayed on the display unit 11. In the case as illustrated in FIG. 4, the gaze point P of the subject is located on the target object Q and the subject is gazing at the target object Q. In this case, the gaze point P is located in the specific region AR including the target object Q. The index is not displayed until last 50 gaze points P counted from when the gaze point P is located in the specific region AR are successively sampled in the specific region AR.

Figure 5:
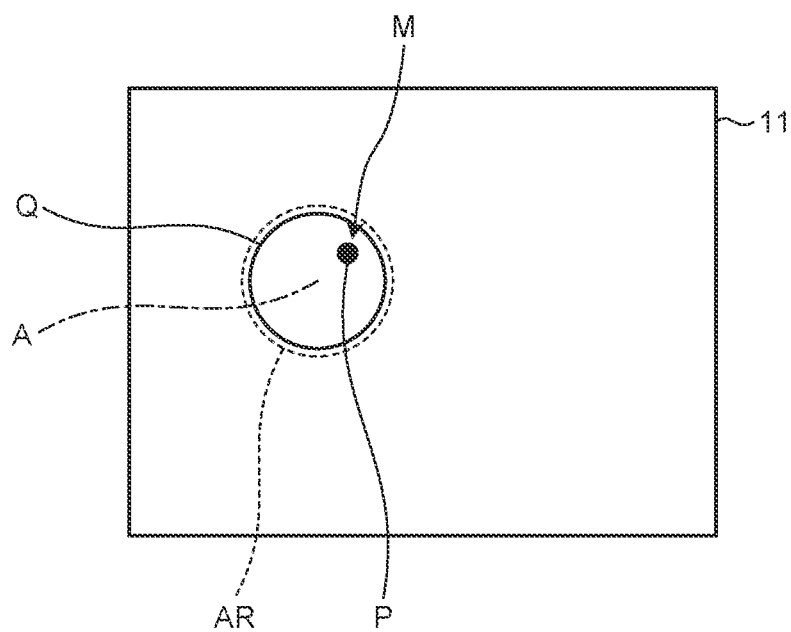
FIG. 5 is a diagram illustrating an example of contents displayed on the display unit.

If 50 gaze points P are successively sampled at positions in the specific region AR, a moving index M is displayed at the position of the gaze point P as illustrated in FIG. 5. The moving index M is displayed at the position of the sampled gaze point every time the gaze point P is sampled. In other words, the moving index M moves in accordance with movement of the gaze point P. In FIG. 5, an example is illustrated in which the moving index M is represented by a black circle, but a display mode of the moving index M is not limited to this example. If the gaze point P is continuously located in the specific region AR, a state in which the moving index M is displayed is continued.

Figure 6:
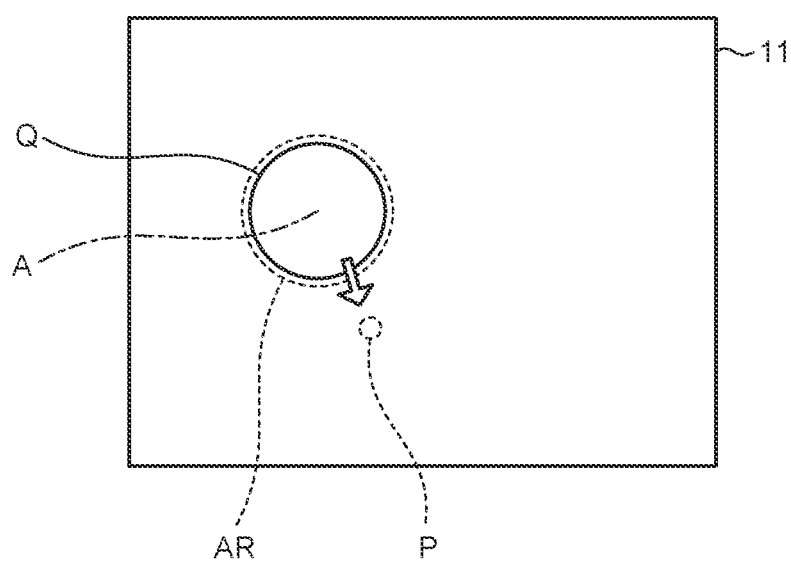
FIG. 6 is a diagram illustrating an example of contents displayed on the display unit.

In contrast, if the gaze point P of the subject is detected outside the specific region AR while the moving index M is being displayed, the first condition is not met because the gaze point is not detected in the specific region AR. In this manner, if it becomes impossible to meet the first condition while the moving index M is being displayed, the display control unit 31 is able to hide the moving index M as illustrated in FIG. 6.

If a second presence time is equal to or larger than a predetermined time as a second index display condition (hereinafter, described as a "second condition"), the display control unit 31 displays an index at the position corresponding to the gaze point on the display unit 11 at the time the second presence time becomes equal to or larger than the predetermined time. The second condition may be that, for example, last 50 gaze points P counted from when the moving index M is displayed are successively sampled in the specific region AR. Further, the index that is displayed when the second condition is met is the fixed index. Furthermore, if the second condition is met, counting of the gaze points P for the second condition is reset.

Figure 7:
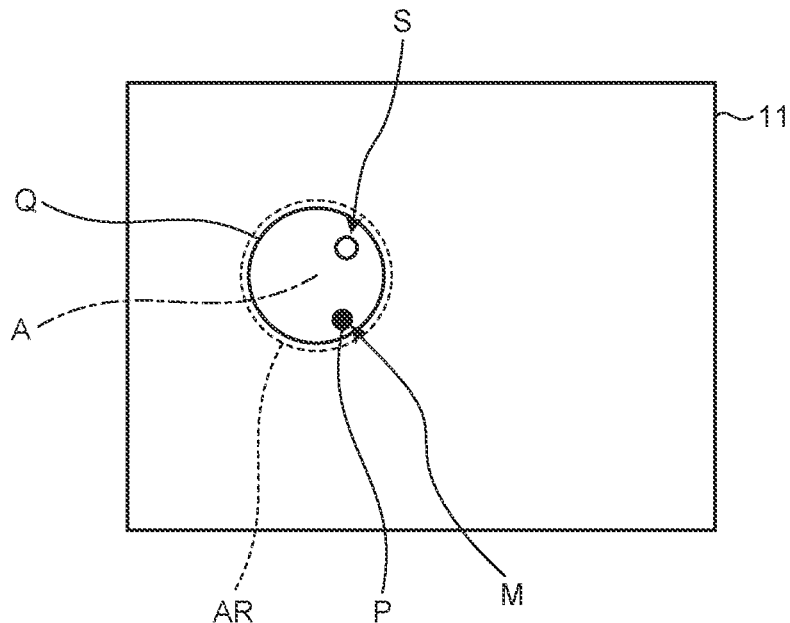
FIG. 7 is a diagram illustrating an example of contents displayed on the display unit.

For example, if last 50 gaze points P are successively sampled in the specific region AR from when the moving index M is displayed as illustrated in FIG. 5, the second condition is met. Therefore, in this case, as illustrated in FIG. 7, the display control unit 31 displays the fixed index S at a position of the 50-th sampled gaze point P. The fixed index S is displayed in a fixed state at the position of the 50-th sampled gaze point P, independent of movement of the gaze point P. In FIG. 7, an example is illustrated in which the fixed index S is represented by a white circle, but a display mode of the fixed index S is not limited to this example. If the gaze point P is continuously located in the specific region AR, the state in which the moving index M is displayed is continued. Due to the display of the single fixed index S, counting of the gaze points P for the second condition is reset.

Figure 8:
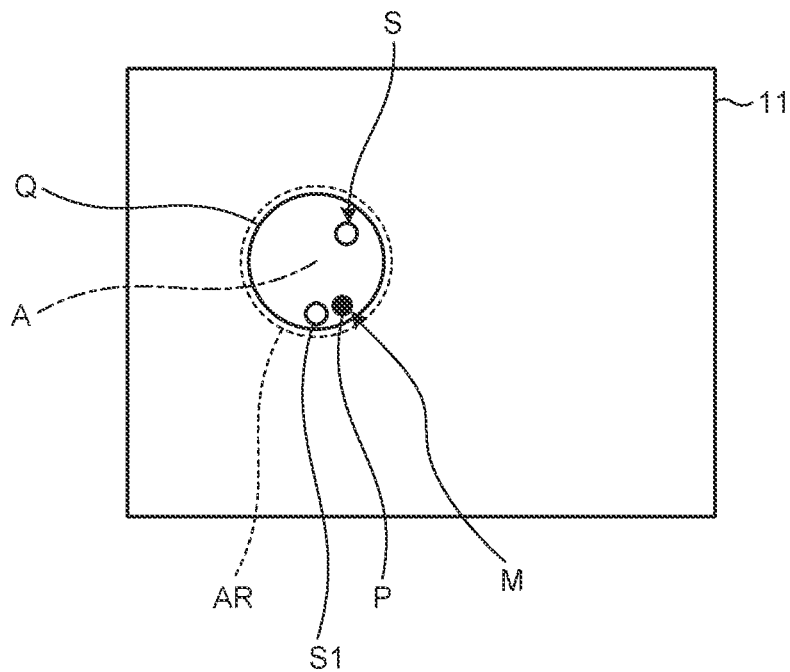
FIG. 8 is a diagram illustrating an example of contents displayed on the display unit.

Therefore, if last 50 gaze points P are successively sampled in the specific region AF from when the moving index M and the fixed index S are displayed, the second condition is met again. In this case, as illustrated in FIG. 8, the display control unit 31 displays a fixed index S1 at a position of the 50-th sampled gaze point P. The fixed index S1 is represented by a white circle similarly to the fixed index S, but is not limited to this example, and a display mode may be different from that of the fixed index S. For example, it may be possible to make setting such that the fixed index S is displayed in response to an instruction to gaze at the target object Q for a while. In this case, it is possible to determine that the visual performance is normal by displaying the fixed index S.

Figure 9:
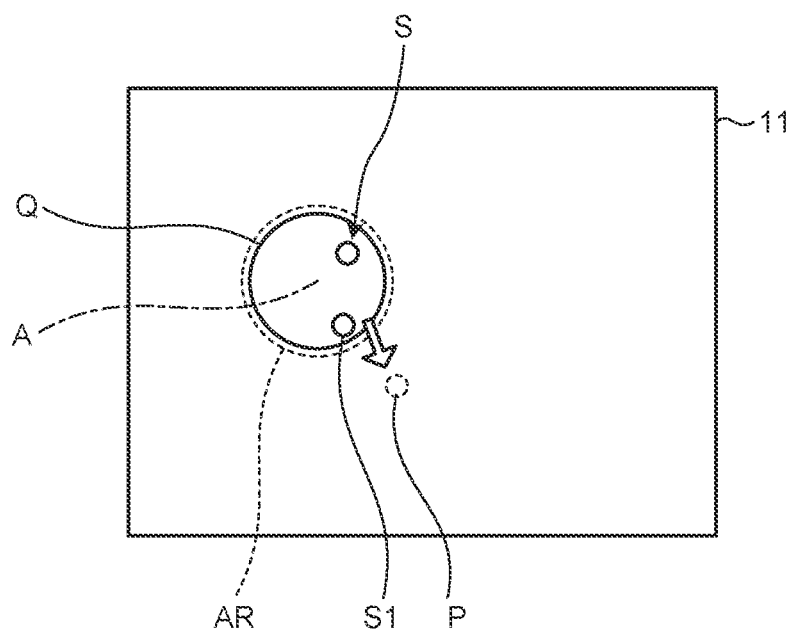
FIG. 9 is a diagram illustrating an example of contents displayed on the display unit.

If the gaze point P of the subject is detected outside the specific region AR while the moving index M and the fixed indices S and S1 are being displayed, the display control unit 31 determines that the first condition is not met because the gaze point is not detected in the specific region AR. If the first condition is not met in the state in which the moving index M is being displayed, the display control unit 31 is able to hide the moving index M as illustrated in FIG. 9. Meanwhile, in this case, the display control unit 31 is able to continuously display the fixed indices S and S1 on the display unit 11. Meanwhile, the fixed indices S and S1 may be hidden similarly to the moving index M.

Figure 10:
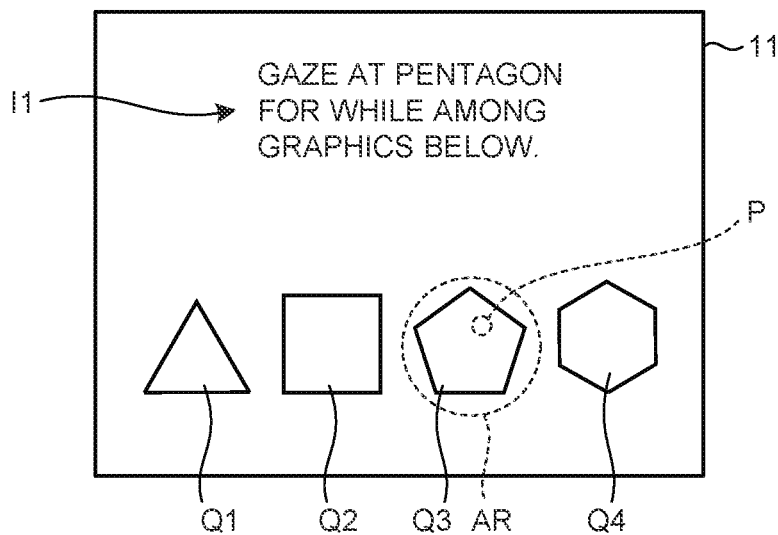
FIG. 10 is a diagram illustrating another example of contents displayed on the display unit.
Figure 11:
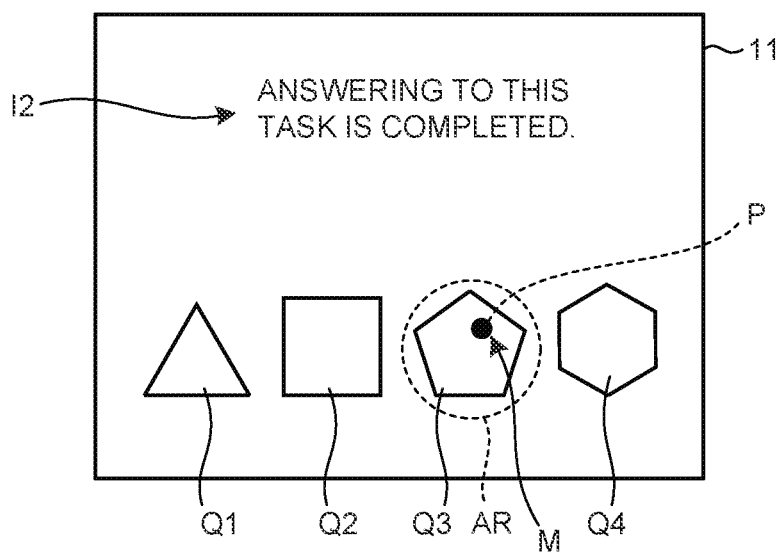
FIG. 11 is a diagram illustrating still another example of contents displayed on the display unit.

FIG. 10 and FIG. 11 are diagrams illustrating other examples of contents displayed on the display unit 11. As illustrated in FIG. 10, the display control unit 31 displays task information I1 and answer target objects Q1 to Q4 for the subject on the display unit 11, for example. In the present embodiment, an example is illustrated in which the task information I1 indicates a task of gazing at a figure of a "pentagon" for a while. The answer target objects include the answer target object Q1 representing a triangle, the answer target object Q2 representing a quadrangle, the answer target object Q3 representing a pentagon, and the answer target object Q4 representing a hexagon. The region setting unit 33 sets the specific region AR in a region including the answer target object Q3 that is a correct answer (pentagon) of the task information I1. The display control unit 31 adopts the first condition as described above (last 50 gaze points P are successively sampled in the specific region AR) as the index display condition. Further, the index that is displayed when the first condition is met is the moving index M.

If the subject gazes at the answer target object Q3 representing a pentagon for a while, the gaze point P of the subject stays within the specific region AR. In this state, if 50 gaze points P are successively sampled at positions in the specific region AR, the moving index M is displayed at the position of the gaze point P as illustrated in FIG. 11. The display control unit 31 causes the display unit 11 to display instruction information I2 indicating that answering to the task is completed, by using the display of the moving index M as a trigger. In this manner, it is possible to adopt, as a condition for completion of answering, a state in which the subject keeps gazing at the target object (the answer target object Q3) until the index (the moving index M) is displayed on the display unit 11. In this case, it is possible to allow the subject to easily recognize the idea of an answering method in which answering is completed by gazing at the answer target object for a while.

Figure 12:
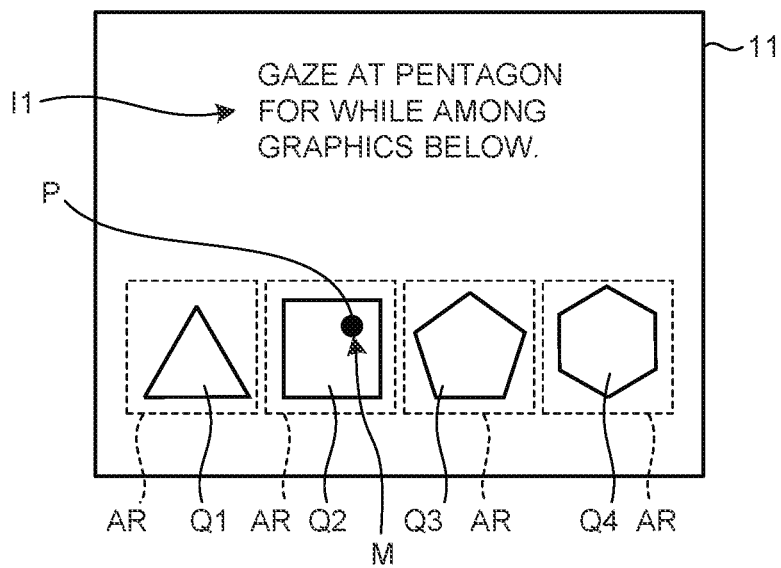
FIG. 12 is a diagram illustrating still another example of contents displayed on the display unit.
Figure 13:
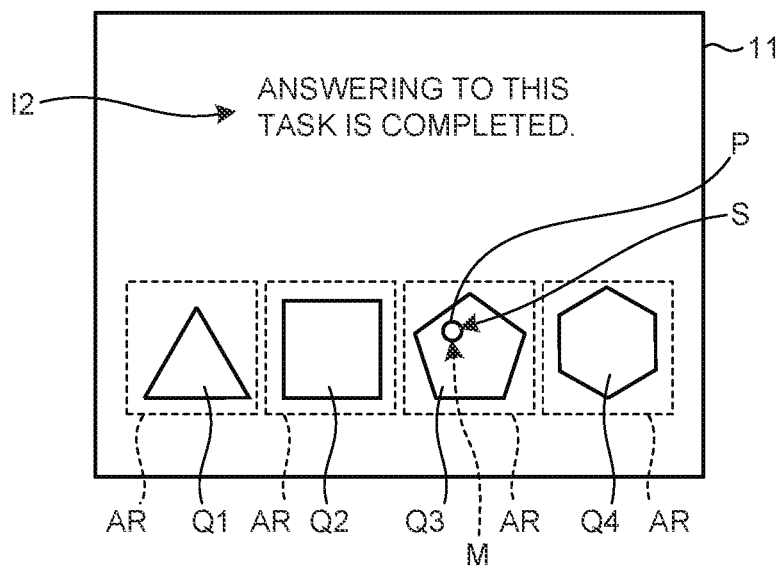
FIG. 13 is a diagram illustrating still another example of contents displayed on the display unit.

FIG. 12 and FIG. 13 are diagrams illustrating contents displayed on the display unit 11. As illustrated in FIG. 12, the display control unit 31 displays the task information I1 and the answer target objects Q1 to Q4 on the display unit 11 similarly to FIG. 10. Meanwhile, in the example illustrated in FIG. 12, the region setting unit 33 sets the specific regions AR in regions including the respective answer target objects Q1 to Q4. The display control unit 31 adopts the first condition (last 50 gaze points P are successively sampled in the specific region AR) and the second condition (last 50 gaze points P are successively sampled in the specific region AR from when the moving index M is displayed) as the index display conditions. Further, the index that is displayed when the first condition is met is the moving index M, and the index that is displayed when the second condition is met is the fixed index S.

Under the conditions as described above, if the subject gazes at any of the answer target objects Q1 to Q4 representing a pentagon for a while, the gaze point P of the subject stays within the specific region AR. In this state, if the first condition is met, in other words, if 50 gaze points P are successively sampled at positions in the specific region AR, the moving index M is displayed at the position of the gaze point P as illustrated in FIG. 12. By displaying the moving index M, if the position that the subject recognizes as a gaze position and the position of the detected gaze point are different for example, it is possible to give the subject an opportunity to correct the position of the gaze point P. For example, in the example illustrated in FIG. 12, the moving index M is displayed on the answer target object Q2. If the subject is recognizing that he/she is gazing at the answer target object Q3 for example, it is possible to correct the position of the gaze point P by moving a viewpoint to the right.

Further, if the subject continuous to gaze at the same region in the state in which the moving index M is displayed at the position corresponding to any of the predetermined answer target objects Q1 to Q4 and the second condition is met, in other words, 50 gaze points P are successively sampled at positions in the specific region, the display control unit 31 may determine that answering is completed and display the fixed index S as illustrated in FIG. 13. Meanwhile, in FIG. 13, a state is illustrated in which the fixed index S overlaps with the moving index M, but embodiments are not limited to this example. Further, the display control unit 31 may display the instruction information I2 indicating that answering to the task is completed by using the display of the fixed index S as a trigger. With this configuration, it is possible to display the moving index M to give the subject an opportunity to correct deviation of the position of the gaze point, determine an answer that is finally gazed at by the subject by using the fixed index S, and terminate the examination. Therefore, it is possible to perform evaluation based on the determined answer.

Figure 14:
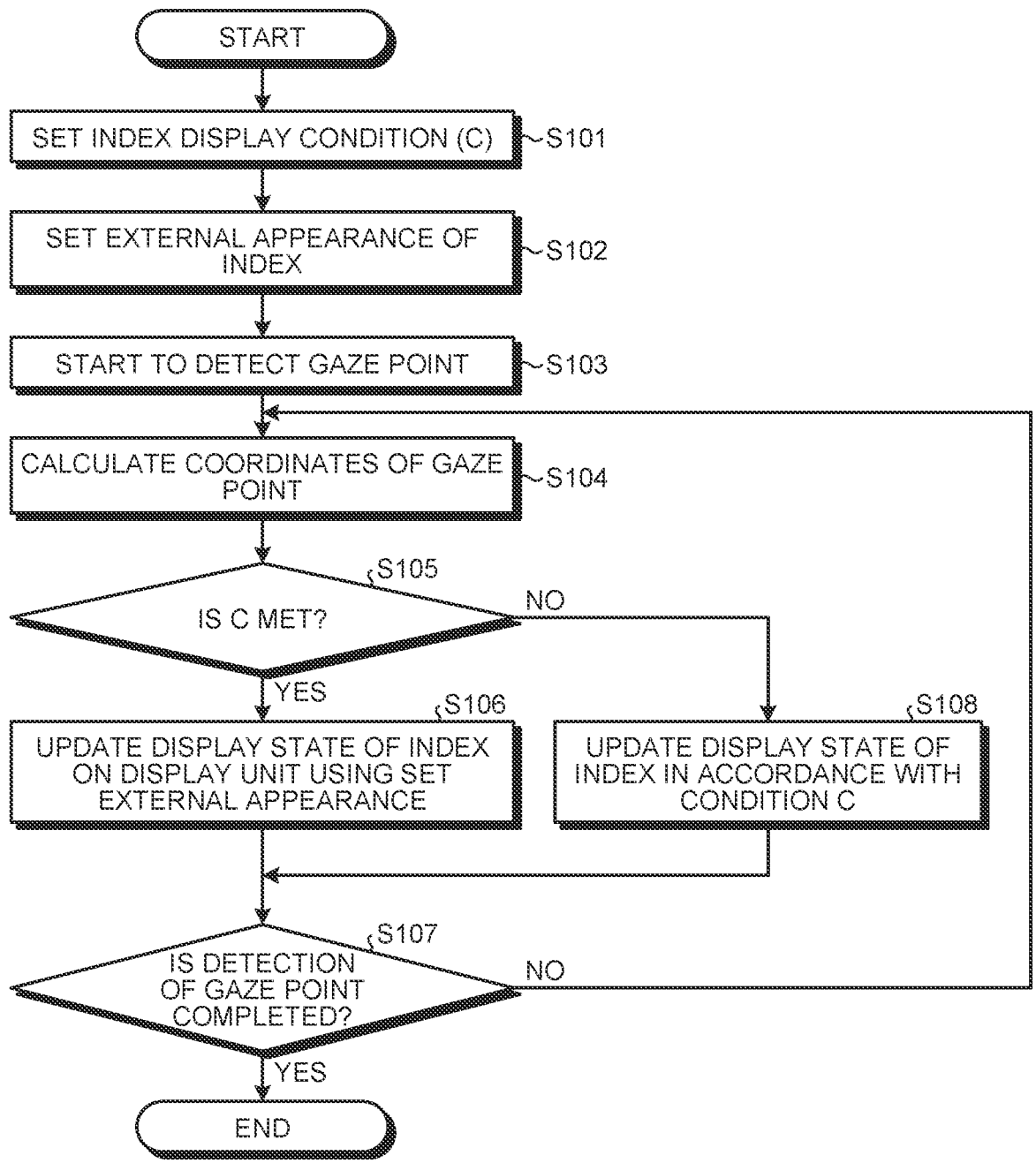
FIG. 14 is a flowchart illustrating an example of a display method according to the present embodiment.

FIG. 14 is a flowchart illustrating an example of the display method according to the present embodiment. In FIG. 14, an example is illustrated in which the moving index M is displayed. As illustrated in FIG. 14, first, an index display condition C is set (Step S101). At Step S101, the display control unit 31 outputs, to the output device 40, information for guiding a user to input the index display condition C via the input device 50 or the like, for example. Then, the index display condition C is set based on a result of input by the input device 50. The index display condition C includes, for example, a position and a range of the specific region AR and a presence time of the gaze point P in the specific region AR. The region setting unit 33 sets the specific region AR on the display unit 11 on the basis of the set index display condition C.

Subsequently, the display control unit 31 sets an external appearance of the index (Step S102). At Step S102, similarly to Step S101, the display control unit 31 outputs, to the output device 40, candidates from among pieces of image data of indices stored in the storage unit 38, and guides the user to input a selection of image data via the input device 50 or the like. Then, the external appearance of the index is set based on a result of input by the input device 50.

Then, detection of the gaze point is started (Step S103). The gaze point detection unit 32 detects the gaze point P of the subject, and calculates the position of the detected gaze point P (Step S104). The determination unit 34 determines whether the gaze point P is present in the specific region AR with the same determination cycle as the sampling cycle of the gaze point detection unit 32 on the basis of the calculated position of the gaze point P, and outputs determination data. The arithmetic unit 35 calculates the presence time data of the gaze point P on the basis of the determination data of the determination unit 34.

The display control unit 31 determines whether the gaze point P meets the index display condition C on the basis of the presence time data calculated by the arithmetic unit 35 (Step S105). If it is determined that the gaze point P meets the index display condition C (Yes at Step S105), the index set at Step S102 is displayed at the position of the gaze point P on the display unit 11 (Step S106). Further, if it is determined that the gaze point P does not meet the index display condition C (No at Step S105), the display mode of the gaze point P is updated in accordance with the index display condition C (Step S108). At Step S108, for example, if the state in which the index of the gaze point P is displayed on the display unit 11 is changed to a state in which the index display condition C is not met, the display control unit 31 clears the displayed index. Further, if the index display condition C is not met while the index of the gaze point P is not being displayed on the display unit 11, the display control unit 31 maintains the state in which the index is not displayed on the display unit 11.

After the process at Step S106 or Step S108, the arithmetic unit 35 determines whether the detection of the gaze point P is completed (Step S107). If it is determined that the detection of the gaze point P is completed (Yes at Step S107), the process is terminated. If it is determined that the detection of the gaze point P is not completed (No at Step S107), the processes from Step S104 are repeated.

FIG. 15 is a flowchart illustrating another example of the display method according to the present embodiment. In FIG. 15, an example is illustrated in which the moving index M and the fixed indices S, S1, . . . are displayed. As illustrated in FIG. 15, first, the index display condition is set and detection of the gaze point P is started (Step S201). At Step S201, a first index display condition (hereinafter, described as an index display condition C1) for displaying the moving index M and a second index display condition (hereinafter, described as an index display condition C2) for displaying the fixed indices S, S1, . . . are set. Here, the index display condition C1 is that if the first presence time in the specific region AR is equal to or larger than a predetermined time, last 50 gaze points P are successively sampled in the specific region AR, for example. Further, the index display condition C2 is that if the second presence time in the specific region AR is equal to or larger than a predetermined time, last 50 gaze points P are successively sampled in the specific region AR from when the moving index M is displayed, for example. Furthermore, if the index display condition C2 is met, counting of the gaze points P is reset. Moreover, at Step S201, external appearances of the moving index M and the fixed indices S, S1, . . . are set. Furthermore, at Step S201, a position and a range of the specific region AR and a presence time of the gaze point P in the specific region AR are set.

Subsequently, the gaze point detection unit 32 detects the gaze point P of the subject, and calculates the position of the detected gaze point P (Step S202). The determination unit 34 determines whether the gaze point P is present in the specific region AR with the same determination cycle as the sampling cycle of the gaze point detection unit 32 on the basis of the calculated position of the gaze point P, and outputs determination data, similarly to the above. The arithmetic unit 35 calculates the presence time data of the gaze point P on the basis of the determination data of the determination unit 34.

The display control unit 31 determines whether the gaze point P is located in the specific region defined by the index display condition C1, on the basis of the presence time data calculated by the arithmetic unit 35 (Step S203). If it is determined that the gaze point P is located in the specific region AR (Yes at Step S203), the display control unit 31 determines whether the predetermined number of repetitions (in this example, 50 repetitions) as defined by the index display condition C1 are performed (Step S204). If it is determined that the predetermined number of repetitions are performed (Yes at Step S204), the display control unit 31 determines whether the moving index is hidden (Step S205). If it is determined that the moving index is hidden (Yes at Step S205), the display control unit 31 displays the moving index M at the position of the gaze point P on the display unit 11 (Step S206).

Further, at Step S203, if it is determined that the gaze point P is not located in the specific region AR (No at Step S203), the arithmetic unit 35 clears the successive number of times of determination for the index display condition C1 (Step S207). Thereafter, the display control unit 31 determines whether the moving index M is displayed (Step S208). If it is determined that the moving index M is displayed (Yes at Step S208), the displayed moving index M is cleared (Step S209), and processes from Step S214 to be described later are performed. If it is determined that the moving index M is not displayed (No at Step S208), processes from Step S215 to be described later are performed.

Furthermore, at Step S204, if it is determined that the gaze point P is located in the specific region AR but the predetermined number of repetitions are not performed (No at Step S204), the processes from Step S215 to be described later are performed.

Moreover, at Step S205, if it is determined that the moving index M is not hidden (is already displayed) (No at Step S205), the display control unit 31 continues to display the moving index M (Step S210).

After the process at Step S206 or S210, the moving index M is displayed on the display unit 11. In this state, the display control unit 31 determines whether the gaze point P is located in the specific region defined by the index display condition C2 (Step S211). In the present embodiment, the specific regions defined by the index display conditions C1 and C2 are the same specific region AR, so that the determination result at Step S211 is the same as the result at Step S203. In contrast, if different specific regions are set for the index display condition C1 and the index display condition C2, determination is performed at Step S211.

At Step S211, if it is determined that the gaze point P is located in the specific region defined by the index display condition C2 (Yes at Step S211), the display control unit 31 determines whether the predetermined number of repetitions (in this example, 50 repetitions) as defined by the index display condition C2 are performed (Step S212). If it is determined that the predetermined number of repetitions are performed (Yes at Step S212), the display control unit 31 displays the fixed index S at the position of the 50-th sampled gaze point P (Step S213). Thereafter, the counter for counting the successive number of times of determination for the index display condition C2 is reset (Step S214).

Furthermore, at Step S211, if it is determined that the gaze point P is not located in the specific region AR (No at Step S211), the processes from Step S214 are performed. Moreover, at Step S212, if it is determined that the gaze point P is located in the specific region AR but the predetermined number of repetitions are not performed (No at Step S212), the processes from Step S215 to be described later are performed.

After No at Step S204, No at Step S208, No at Step S212, or the process at Step S214, the arithmetic unit 35 determines whether the detection of the gaze point P is completed (Step S215). If it is determined that detection of the gaze point P is completed (Yes at Step S215), the process is terminated. If it is determined that detection of the gaze point P is not completed (No at Step S215), the processes from Step S202 are repeated.

As described above, the display apparatus 100 according to the present embodiment includes the display unit 11 that displays a predetermined target object to be gazed at by a subject, the gaze point detection unit 32 that detects positions of gaze points of the subject who observes the display unit 11, the region setting unit 33 that sets the specific region AR corresponding to the predetermined target object, the determination unit 34 that determines whether each of the gaze points is present in the specific region AR, the arithmetic unit 35 that calculates gaze point data on the basis of a determination result of the determination unit 34, and the display control unit 31 that displays an index at a position corresponding to a gaze point on the display unit 11 if the gaze point data meets the index display condition.

The display method according to the present embodiment includes displaying a predetermined target object to be gazed at by a subject on the display unit 11, detecting positions of gaze points of the subject who observes the display unit 11, setting the specific region AR corresponding to the predetermined target object, determining whether each of the gaze points is present in the specific region AR, calculating gaze point data on the basis of a determination result, and displaying an index at a position corresponding to a gaze point on the display unit 11 if the gaze point data meets an index display condition.

A display program according to the present embodiment causes a computer to perform a process of displaying a predetermined target object to be gazed at by a subject on the display unit 11, a process of detecting positions of gaze points of the subject who observes the display unit 11, a process of setting the specific region AR corresponding to the predetermined target object, a process of determining whether each of the gaze points is present in the specific region AR, a process of calculating gaze point data on the basis of a determination result, and a process of displaying an index at a position corresponding to a gaze point on the display unit 11 if the gaze point data meets an index display condition.

According to the present embodiment, if the gaze point data meets the index display condition, the display control unit 31 causes the display unit 11 to display the index at the position corresponding to the gaze point P. By allowing the subject to recognize a position gazed at by the subject in real time, if a position that the subject recognizes as a gaze position and a position of the detected gaze point are different for example, it is possible to allow the subject to recognize deviation between the gaze position recognized by the subject and the position of the detected gaze point, and give the subject an opportunity to correct deviation of the position of the gaze point P. With this configuration, it is possible to eliminate deviation between the gaze position recognized by the subject and the position of the detected gaze point, and display the gaze point of the subject.

In the display apparatus 100 according to the present embodiment, the gaze point data includes a first presence time in which the gaze points are successively present in the specific region AR, a predetermined index display condition includes a first index display condition, and the first index display condition is that if the first presence time is equal to or larger than a predetermined time, the moving index M is displayed as the index at a position corresponding to a gaze point on the display unit every time the position of the gaze point is detected. By displaying the moving index M, it is possible to allow the subject to recognize deviation between the gaze position recognized by the subject and the position of the detected gaze point. With this configuration, it is possible to give the subject an opportunity to correct deviation of the position of the gaze point.

In the display apparatus 100 according to the present embodiment, the gaze point data includes a second presence time in which the gaze points are successively present in the specific region AR, the predetermined index display condition includes a second index display condition, and the second index display condition is that if the second presence time is equal to or larger than a predetermined time, the fixed index S is displayed as the index at a position corresponding to a gaze point on the display unit 11 at the time the gaze point data meets the second index display condition. By displaying the fixed index S, it is possible to recognize the final gaze point of the subject.

In the display apparatus 100 according to the present embodiment, the second index display condition is that the fixed index S is displayed when the second presence time is equal to or larger than a predetermined time after the moving index is displayed under the first index display condition. With this configuration, it is possible to display the moving index M, give the subject an opportunity to correct deviation of the position of the gaze point, determine, by the fixed index S, an answer that is finally gazed at by the subject, and terminate the examination. Therefore, it is possible to perform evaluation based on the determined answer.

The technical scope of the present disclosure is not limited to the embodiments as described above, but may be appropriately changed within a scope not departing from the gist of the present disclosure. For example, in each of the embodiments as described above, the example has been described in which the display apparatus 100 is used as a display apparatus that gives feedback on a state of visual performance to the subject, but the present disclosure is not limited to this example. For example, the display apparatus 100 may be used to evaluate a development disability, cognitive impairment, and brain impairment of the subject.

Furthermore, in the present embodiment, the example has been described in which the fixed index is displayed after the moving index is displayed, but the present disclosure is not limited to this example. For example, it may be possible to display the moving index without displaying the fixed index. Further, it may be possible to display the fixed index without displaying the moving index.

A display apparatus, a display method, and a display program according to the present disclosure may be adopted to, for example, a line-of-sight detection apparatus.

According to the present disclosure, it is possible to provide a display apparatus, a display method, and a display program capable of giving feedback on a state of visual performance to a subject.

What is claimed is:
1. A display apparatus comprising:
   a display unit that displays a predetermined target object to be gazed at by a subject;

a gaze point detection unit that detects a position of a gaze point of the subject who observes the display unit;

a region setting unit that sets a specific region corresponding to the predetermined target object;

a determination unit that determines whether the gaze point is present in the specific region;

an arithmetic unit that calculates gaze point data on the basis of a determination result of the determination unit; and a display control unit that, in a period in which the gaze point detection unit is detecting the position of the gaze point of the subject, if the gaze point data is successively present in the specific region for a first presence time or longer, displays a moving index at a position corresponding to the gaze point of the subject on the display unit, and after the moving index is displayed, if the gaze point data is successively present in the specific region for a second present time or longer, displays a fixed index at the position corresponding to the gaze point of the subject on the display unit, a display mode of the fixed index being different from a display mode of the moving index, wherein the display control unit that, after the moving index is displayed, if the gaze point of the subject is outside the specific region, stops displaying the moving index, and after the fixed index is displayed, if the gaze point of the subject is outside the specific region, continues to display the fixed index.

2. The display apparatus according to claim 1, wherein if the fixed index is displayed, the display control unit displays an instruction indicating that answering to a task is completed.

3. A display method comprising:

displaying a predetermined target object to be gazed at by a subject on a display unit;

detecting a position of a gaze point of the subject who observes the display unit;

setting a specific region corresponding to the predetermined target object;

determining whether the gaze point is present in the specific region;

calculating gaze point data on the basis of a determination result; and displaying, in a period in which a position of the gaze point of the subject is being detected, if the gaze point data is successively present in the specific region for a first presence time or longer, a moving index at a position corresponding to the gaze point of the subject on the display unit, and after the moving index is displayed, if the gaze point data is successively present in the specific region for a second present time or longer, a fixed index at the position corresponding to the gaze point of the subject on the display unit, a display mode of the fixed index being different from a display mode of the moving index, wherein, after the moving index is displayed, if the gaze point of the subject is outside the specific region, displaying the moving index is stopped, and after the fixed index is displayed, if the gaze point of the subject is outside the specific region, displaying the fixed index is continued.

4. A non-transitory computer readable recording medium storing therein a display program that causes a computer to execute:

a process of displaying a predetermined target object to be gazed at by a subject on a display unit;

a process of detecting a position of a gaze point of the subject who observes the display unit;

a process of setting a specific region corresponding to the predetermined target object;

a process of determining whether the gaze point is present in the specific region;

a process of calculating gaze point data on the basis of a determination result; and a process of displaying, in a period in which the position of the gaze point of the subject is being detected, if the gaze point data is successively present in the specific region for a first presence time or longer, a moving index at a position corresponding to the gaze point of the subject on the display unit, and after the moving index is displayed, if the gaze point data is successively present in the specific region for a second present time or longer, a fixed index at the position corresponding to the gaze point of the subject on the display unit, a display mode of the fixed index being different from a display mode of the moving index, wherein, after the moving index is displayed, if the gaze point of the subject is outside the specific region, displaying the moving index is stopped, and after the fixed index is displayed, if the gaze point of the subject is outside the specific region, displaying the fixed index is continued.

* * * * *